United States Patent [19]

Fürst et al.

[11] 4,026,918
[45] May 31, 1977

[54] D-HOMOSTEROIDS

[76] Inventors: Andor Fürst, 14 Magnolienpark, Basel; Marcel Müller, 10 Quellenweg, Frenkendorf; Leo Alig, 76 Heidenlochstrasse, Liestal; Peter Keller, 10 Bahnhofstrasse, Therwil, all of Switzerland; Ulrich Kerb, 8 Waitzstrasse; Rudolf Wiechert, 8a Petzowerstrasse, both of Berlin, Germany; Klaus Kieslich, 4 Strasse zum Lowen, Berlin 39, Germany; Karl Petzoldt, 10 Flachsweg, Berlin 38, Germany

[22] Filed: Sept. 20, 1974

[21] Appl. No.: 507,882

[30] Foreign Application Priority Data

Sept. 26, 1973 Germany .......................... 2349023

[52] U.S. Cl. .................. 260/488 B; 195/51 S; 195/51 A; 260/293.56; 260/295.5 P; 260/340.5; 260/340.7; 260/340.9; 260/348 A; 260/348 C; 260/408; 260/410; 260/456 R; 260/457; 260/468 R; 260/476 C; 260/482 R; 260/484 B; 260/484 R; 260/485 F; 260/485 G; 260/485 H; 260/487; 260/586 E; 260/946; 260/485 L; 260/486 H; 260/486 R; 424/214; 424/266; 424/267; 424/305; 424/308; 424/278; 424/311; 424/312; 424/303; 424/313; 424/331

[51] Int. Cl.[2] ......................................... C07J 63/00

[58] Field of Search ........... 260/457, 488 B, 586 E, 260/476 C, 946, 410, 457, 485 F, 485 G, 485 H, 485 L, 486 R, 486 H, 468 R, 408

[56] References Cited

UNITED STATES PATENTS

| | | | |
|---|---|---|---|
| 2,822,381 | 2/1958 | Dodson et al. | 260/488 B |
| 2,860,158 | 11/1958 | Clinton | 260/488 B |
| 3,076,023 | 1/1963 | Kaspar et al. | 260/586 E |
| 3,492,338 | 1/1970 | Hader et al. | 260/488 B |
| 3,939,193 | 2/1976 | Alig et al. | 260/488 B |

OTHER PUBLICATIONS

Chem. Abstracts, 80:37392g.
Chem. Abstracts, 49:6299d.
Chem. Abstracts, 52:11980a.

*Primary Examiner*—Vivian Garner
*Attorney, Agent, or Firm*—Samuel L. Welt; George M. Gould

[57] ABSTRACT

Novel D-homosteroids of the formula

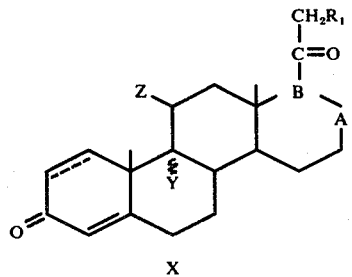

are disclosed. The novel D-homosteroids exhibit anti-inflammatory activity and are useful intermediates for the synthesis of anti-inflammatory D-homosteroids.

8 Claims, No Drawings

D-HOMOSTEROIDS

Description of the Invention

The present invention relates to new D-homosteroids, a process for their preparation, as well as their utility as intermediates and/or medicinals.

The new D-homosteroids are represented by general formula I.

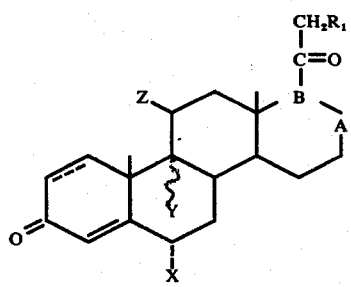

wherein the linkage ≈≈≈ is a single or double bond, the grouping fluoro,

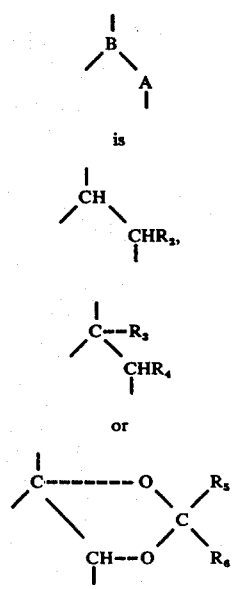

wherein $R_2$ is hydrogen or methyl, $R_3$ is hydroxy or acyloxy, $R_4$ is methyl, hydroxy or acyloxy, $R_5$ is hydrogen or lower alkyl and $R_6$ is lower alkyl or phenyl, and wherein $R_1$ is hydrogen, fluoro, chloro, hydroxy or esterified hydroxy, X is hydrogen, fluoro or methyl and Y and Z together is a carbon-carbon bond or an epoxy group, or Y is hydrogen and Z is α-hydroxy, or α-lower alkanoyloxy; or Z is α-hydroxy, α-lower alkanoyloxy or hydrogen when both $R_1$ and $R_2$ are substituents other than hydrogen.

With regard to the 21-hydroxy group, $R_1$ is preferably acyloxy having 1 to 16 carbon atoms in the acyl residue, sulfate or phosphate. For example, suitable acyloxy groups are derived from straight or branched, saturated or unsaturated aliphatic mono- or dicarboxylic acids, which, for example, can be substituted in the usual way by hydroxy groups, amino groups or halogen atoms. Cycloaliphatic, aromatic, mixed aromatic-aliphatic or hetrocyclic acids, which can be likewise substituted in the usual way, are also suitable as the residue of the acyloxy groups.

For example, formyloxy, acetoxy, propionyloxy, butyryloxy, pentanoyloxy, hexanoyloxy, octanoyloxy, undecanoyloxy, dimethylacetoxy, trimethylacetoxy, diethylacetoxy, tert.-butylacetoxy, benzoyloxy, phenacetyloxy, cyclopentylpropionyloxy, hydroxyacetoxy, monochloroacetoxy, dichloroacetoxy, trichloroacetoxy, and dimethylaminoacetoxy, trimethylaminoacetoxy, diethylaminoacetoxy, piperidinoacetoxy, nicotinoyloxy, ω-carboxypropionyloxy and ω-carboxypentanoyloxy are suitable acyloxy groups.

For the preparation of water soluble compounds, the 21-acyl compounds having a basic nitrogen group in the acyl residue can be transformed into the corresponding acid addition salts, for example, the hydrochloride, hydrobromide, sulfate, phosphate, oxalate, tartrate or maleate. Further, the 21-carboxylic acid monoesters as well as the sulfuric and phosphoric esters can be converted into their alkali salts, for example, the sodium or potassium salts, to increase water solubility.

With regard to the acyloxy groups represented by $R_3$ and $R_4$ such groups preferably contain 1 to 8 carbon atoms in the acyl residue. Alkanoyloxy groups, as for example, formyl, acetoxy, propionyloxy, butyryloxy or hexanoyloxy are especially preferred acyloxy groups.

Among the D-homosteroids of general formula I wherein $R_5$ and/or $R_6$ denotes a lower alkyl group, the preferred compounds should be understood to be those whose alkyl groups, $R_5$ and $R_6$, possess 1 to 4 carbon atoms. The methyl, ethyl, propyl and butyl groups are examples of the named alkyl groups, $R_5$ and $R_6$.

Among the lower alkanoyloxy groups Z the preferred groups should be understood to be those having 1 to 6 carbon atoms. The formyloxy, acetoxy, propionyloxy, butyryloxy and trimethylacetoxy groups are examples of the named alkanoyloxy group.

The new D-homosteroids of general formula I can be prepared in a known way by means of a process which is characterized by a. oxidizing a compound of general formula II

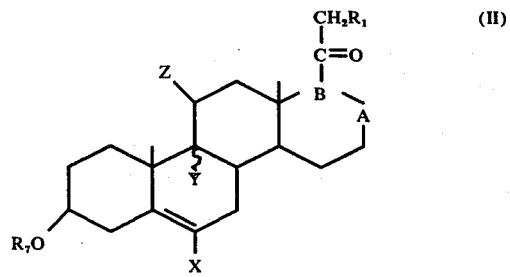

wherein X, Y, Z, —A—B< and $R_1$ have the same meaning as in formula I and $R_7$ is hydrogen or a lower acyl residue, preferably having 1 to 6 carbon atoms, to yield the corresponding 3-keto-$\Delta^4$-steroid whereby a 3-acyloxy group present in the compound of formula II is, if required, saponified prior to the oxidation, or b. eliminating HV from a compound of the general formula III

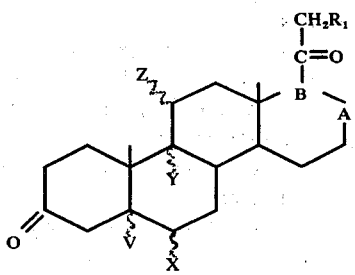

wherein X, Y, Z, —A—B< and $R_1$ have the same meaning as in formula I and V is hydroxy or bromo, or c. hydroxylating in the 11α- or 11β-position a compound of general formula IV

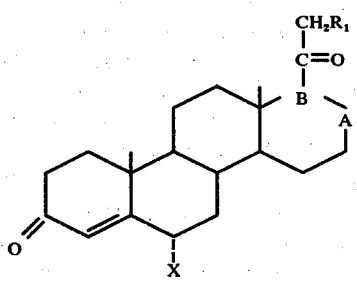

wherein X, —A—B< and $R_1$ have the same meaning as in formula I, with 11-hydroxylating microorganisms, splitting, if necessary, the 11-hydroxy group, adding hypochlorous or hypobromous acid to the formed $\Delta^{9(11)}$-steroid of general formula I and converting the formed 11β-hydroxy-9α-halosteroid by treatment with base to the 9,11-epoxysteroid of general formula I, or d. adding hydroxy groups to the $\Delta^{17}$-double bond of a compound of general formula V

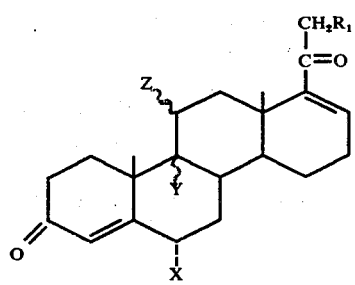

wherein X, Y, Z and $R_1$ have the same meaning as in formula I, to prepare the D-homosteroids of general formula I wherein $R_3$ and $R_4$ represent hydroxy groups, or e. exchanging the substituent W of a compound of general formula VI

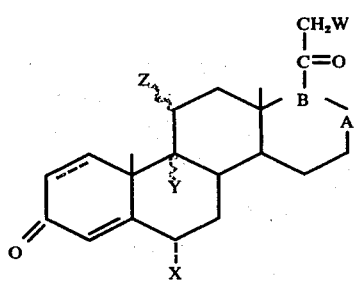

wherein ====, X, Y, Z and —A—B< have the same meaning as in formula I and W is alkylsulfonyloxy, arylsufonyloxy, bromo or iodo, by hydrogen, chloro, fluoro, acyloxy or a phosphate residue, or f. treating compounds of general formula VII

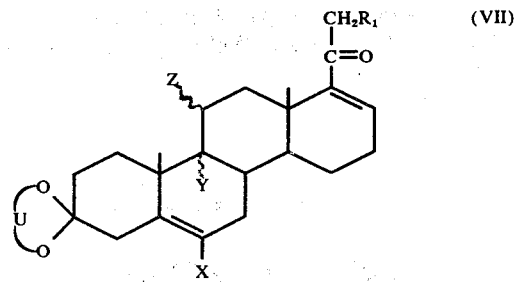

wherein X, Y, Z and $R_1$ have the same meaning as in formula I and U is an alkylene residue, preferably a branched alkylene residue having 3 to 10 carbon atoms, for example, the 2,2-dimethylpropyl or phenyl residue, with a methylmagnesium halide or lithium dimethylcopper; if necessary, converting the 20-keto group to the 20-enolacylate by treating with acylchlorides or acylbromides and epoxidizing the latter with peracid, hydrolysing the obtained reaction product by attacking with acid to prepare 17-methyl-D-homosteroids of formula I and, if desired, dehydrogenating the D-homo-$\Delta^4$-steroids of general formula I, obtained by means of the process variations a to f, in the 1,2-position; and/or splitting hydrolytically the existing ester or ketal groups and/or esterifying the existing hydroxy groups or condensing the existing hydroxy groups with carbonyl compounds of general formula, $R_5R_6CO$, wherein $R_5$ and $R_6$ have the above-named meaning.

In accordance with the process of this invention, the following examples of 9,11-unsubstituted D-homosteroids, as well as the 21-acetate, 21-valerate, 21-capronate, and the sodium salt of the 21-monosulfate or 21-phosphate esters of these compounds can be prepared:

a. 21-hydroxy-17α-methyl-D-homo-pregnene-3,20-dione.

b. 21-hydroxy-17α-methyl-D-homo-1,4-pregnadiene-3,20-dione.

c. 6α-fluoro-21-hydroxy-17α-methyl-D-homo-4-pregnene-3,20-dione.

d. 6α-fluoro-21-hydroxy-17α-methyl-D-homo-1,4-pregnadiene-3,20-dione.

e. 21-hydroxy-6α,17α-dimethyl-D-homo-4-pregnene-3,20-dione.

f. 21-hydroxy-6α,17α-dimethyl-D-homo-1,4-pregnadiene-3,20-dione.

g. 17aα,21-dihydroxy-17α-methyl-D-homo-4-pregnene-3,20-dione.

h. 21-hydroxy-17aα-acetoxy,17α-methyl-D-homo-4-pregnene-3,20-dione.

i. 17aα,21-dihydroxy-17α-methyl-D-homo-1,4-pregnadiene-3,20-dione.

j. 6α-fluoro-17aα,21-dihydroxy-17α-methyl-D-homo-4-pregnene-3,20-dione.

k. 6α-fluoro-21-hydroxy-17aα-acetoxy-17α-methyl-D-homo-4-pregnene-3,20-dione.

l. 6α-fluoro-17aα,21-dihydroxy-17α-methyl-D-homo-1,4-pregnadiene-3,20-dione.

m. 6α-fluoro-21-hydroxy-17aα-acetoxy-17α-methyl-D-homo-1,4-pregnadiene-3,20-dione.

n. 6α-fluoro-17α,17aα,21-trihydroxy-D-homo-4-pregnene-3,20-dione.

o. 6α-fluoro-21-hydroxy-17α,17aα-isopropylidenedioxy-D-homo-4-pregnene-3,20-dione.

p. 6α-fluoro-17α,17aα,21-trihydroxy-D-homo-1,4-pregnadiene-3,20-dione.

q. 6α-fluoro-21-hydroxy-17α,17aα-isopropylidenedioxy-D-homo-1,4-pregnadiene-3,20-dione.

Further, the following 9,11-unsubstituted D-homosteroids can also be prepared in accordance with the processes of this invention:

a. 6α,21-difluoro-17α-methyl-D-homo-4-pregnene-3,20-dione.

b. 6α,fluoro-21-chloro-17α-methyl-D-homo-4-pregnene-3,20-dione.

c. 6α,21-difluoro-17α-methyl-D-homo-1,4-pregnadiene-3,20-dione.

d. 6α-fluoro-21-chloro-17α-methyl-D-homo-1,4-pregnadiene-3,20-dione.

e. 6α,21-difluoro-17α,17aα-isopropylidenedioxy-D-homo-4-pregnene-3,20-dione.

f. 6α-fluoro-21-chloro-17α,17aα-isopropylidenedioxy-D-homo-4-pregnene-3,20-dione.

g. 6α,21-difluoro-17α,17aα-isopropylidenedioxy-D-homo-1,4-pregnadiene-3,20-dione.

h. 6α-fluoro-21-chloro-17α,17aα-isopropylidenedioxy-D-homo-1,4-pregnadiene-3,20-dione.

In addition, in accordance with the processes of this invention, the following examples of 11α-hydroxy-D-homosteroids of general formula I and the 11-acetate, 21-acetate and 11,21-diacetate of these compounds can be prepared:

a. 11α,21-dihydroxy-D-homo-4-pregnene-3,20-dione.

11α,21-dihydroxy-D-homo-1,4-pregnadiene-3,20-dione.

c. 6α-fluoro-11α,21-dihydroxy-17α-methyl-D-homo-4-pregnene-3,20-dione.

d. 6α-fluoro-11α,21-dihydroxy-17α-methyl-D-homo-1,4-pregnadiene-3,20-dione.

e. 11α,17aα,21-trihydroxy-17α-methyl-D-homo-4-pregnene-3,20-dione.

f. 11α,17aα21-trihydroxy-17α-methyl-D-homo-1,4-pregnadiene-3,20-dione.

g. 6α-fluoro-11α,17aα,21-trihydroxy-17α-methyl-D-homo-4-pregnene-3,20-dione.

h. 6α-fluoro-11α,17aα,21-trihydroxy-17α-methyl-D-homo-1,4-pregnadiene-3,20-dione.

i. 6α-fluoro-11α,21-dihydroxy-17α,17aα-isopropylidenedioxy-D-homo-4-pregnene-3,20-dione.

j. 6α-fluoro-11α,21-dihydroxy-17α,17aα-isopropylidenedioxy-D-homo-1,4-pregnadiene-3,20-dione.

Also in accordance with the processes of this invention, the following examples of 9,11-unsaturated D-homosteroids of general formula I and their 21-acetates and 21-trimethylacetates can be prepared:

a. 21-hydroxy-D-homo-4,9(11)-pregnadiene-3,20-dione.

b. 21-hydroxy-D-homo-1,4,9(11)-pregnatriene-3,20-dione.

c. 6α-fluoro-21-hydroxy-17α-methyl-D-homo-4,9(11)-pregnadiene-3,20-dione.

d. 6α-fluoro-21-hydroxy-17α-methyl-D-homo-1,4,9(11)-pregnatriene-3,20-dione.

e. 6α-fluoro-21-hydroxy-17α,17aα-isopropylidenedioxy-D-homo-4,9(11)-pregnadiene-3,20-dione.

f. 6α-fluoro-21-hydroxy-17α,17aα-isopropylidenedioxy-D-homo-1,4,9(11)-pregnatriene-3,20-dione.

Further, 6α-fluoro-17α,17aα-isopropylidenedioxy-D-homo-4,9(11)-pregnadiene-3,20-dione and 6α-fluoro-17α,17aα-isopropylidenedioxy-D-homo-1,4,9(11)-pregnatriene-3,20-dione can be prepared in accordance with the processes of this invention.

Also, the following examples of 9,11-epoxy-D-homosteroids and their 21-acetates and 21-trimethylacetates can be prepared in accordance with the processes of this invention:

a. 21-hydroxy-9β,11β-epoxy-D-homo-1,4-pregnadiene-3,20-dione.

b. 6α-fluoro-21-hydroxy-9β,11β-epoxy-17α-methyl-D-homo-1,4-pregnadiene-3,20-dione.

c. 6α-fluoro-21-hydroxy-9β,11β-epoxy-17α,17aα-isopropylidenedioxy-D-homo-1,4-pregnadiene-3,20-dione.

It was already mentioned, that one can prepare the D-homosteroids of general formula I by means of known processes.

One can also apply microbiological methods as well as pure chemical methods to perform the processes according to variant (a). For example, one can ferment the compounds of formula II, in which $R_7$ is hydrogen or a lower acyl residue, under the usual conditions with microorganisms of the genus Flavobacterium (for example, *F. dehydrogenans, F. buccalis* or *F. fulvium*) and obtain the corresponding 3-keto-$\Delta^4$-steroids of general formula I saturated in the 1,2-position. Under these conditions, acyloxy groups in the 3-position and, if attached to the 21-positions, are saponified during the transformation.

For these microbiological oxidations, one can apply, instead of microorganisms of the genus Flavobacterium, other microorganisms, for example, strains of the genus Micrococcus (for example, *Micrococcus dehydrogenans*), Corynebacterium (for example, *Corynebacterium mediolanum*), Norcardia or Fusarium (for example, *Fusarium solani*). As is known, the oxidation of the 3-hydroxy group and the isomerization of the $\Delta^5$-double bond by these microorganisms often additionally leads to a $\Delta^1$-dehydrogenation.

Such compounds of general formula II in which the substituent X is hydrogen are especially suited for the microbiological oxidation according to process variant (a).

To accomplish the oxidation according to process variant (a) by means of pure chemical methods, it is necessary to cleave the acyl residue, if present in the 3-position, in the usual way before oxidation. Further, it is desirable to protect existing free hydroxyl groups in the 17α- and/or 21-position by acylation.

The chemical oxidation of compounds of general formula II also occurs by known methods, such as the Oppenauer oxidation e.g., with either aluminum isopropylate or aluminum tert.-butylate in a ketone solvent, such as acetone or preferably cyclohexanone.

The process according to process variant (b) can also be accomplished in another known way. For example, one can eliminate hydrogen bromide from compounds of general formula III by treatment with bases (as for example, triethylamine, potassium carbonate, calcium carbonate, sodium acetate and lithium carbonate). Further, one can apply inorganic or organic acids, for example, formic acid, acetic acid, oxalic acid, hydrochloric acid, phosphoric acid and sulfuric acid to eliminate hydrogen bromide and, especially water. The latter elimination will isomerize substituent X (fluoro or methyl) attached to the β-position.

To effect the process according to variant (c), one applies the usual fermentation with 11α- or 11β-hydroxylation microorganisms. For 11α-hydroxylation, one applies preferably, strains of fungi of the genus Aspergillus (for example, *Aspergillus ochraceus*) as the microorganism. For 11β-hydroxylation, for example, strains of fungi of the genus Curvularia (for example, *Curvulaira lunata*), Cunninghamella (for example, *Cunninghamella baineri, Cunninghamella elegans, Cunninghamella echinolata* and *Cunninghamella blakesleeana*), Absidia (for example, *Absidia orchidis* and *Absidia coerula*), Helmintosporium, Rhizoctonia (for example, *Rhizoctonia solani*), Verticillium (for example, *Verticillium theobromae*), Stachylidium (for example, *Stachylidium bicolor*), Pellicularia (for example, *Pellicularia filamentosa*) or Colletotrichum (for example, *Colletotrichum pisi*) can be applied. Fermentation with these microorganisms can be accomplished under the usual conditions. The acyl group attached to the 21-position is readily cleaved during this transformation. The process variant (c) is preferably accomplished with such compounds of general formula IV, which bear a hydroxy group or an acyloxy group at the 21-position. The elimination of the 11-hydroxy group attached by the microbiological hydroxylation can also be accomplished by means of known methods, for example, by treatment of 11-hydroxy-steroids with thionyl chloride, methanesulfonyl chloride or trimethylacetyl chloride in the presence of base, such as pyridine. This method is suitably applied to starting compounds of general formula IV, which do not bear a free hydroxyl group in the 21-position. It is expected that the dehydration of the 11β-hydroxy steroids would furnish higher yields of the reaction product than elimination from the corresponding 11α-hydroxy steroid.

The resultant $\Delta^{9(11)}$-steroids can be converted into the 9,11-epoxide by known methods, for example, by treating the $\Delta^{9(11)}$-steroids with N-chloroacylamide (for example, N-chloroacetamide), N-bromoacylamide (for example, N-bromoacetamide), N-chloroacylimide (for example, N-chlorosuccinimide), or N-bromoacylimide (for example, N-bromosuccinimide) and converting the so obtained 9α-halo-11β-hydroxysteroids to the corresponding 9β,11β-epoxides by treatment with base (for example, sodium hydroxide, potassium hydroxide, potassium carbonate, sodium acetate, potassium acetate and pyridine).

The process according to process variant (d) can be carried out under the same conditions as one ordinarily applies for the conversion of $\Delta^{16}$-steroids to 16,17-dihydroxy steroids. For example, a compound of general formula V may be reacted with osmium tetroxide or potassium permanganate.

The process according to process variant (e) can be carried out under the same conditions, which one ordinarily applies to substitute, in an organic compound, a bromine atom or iodine atom, an alkylsulfonyl group (preferably a methanesulfonyl group) or an arylsulfonyl group (preferably a p-toluenesulfonyl group) by hydrogen, fluorine, chlorine, an acyloxy group or a phosphate residue. For example, one can reduce compounds of general formula VI wherein W is an iodine atom or a p-toluenesulfonyl group by reaction with zinc dust and obtain the corresponding 21-unsubstituted D-homosteroid of general formula I. Further, one can treat compounds of general formula VI in a polar solvent with alkali metal halides (preferably potassium hydrogen difluoride or lithiumchloride) or an alkali metal acylate (as for example, sodium acetate) and obtain the corresponding 21-fluoro-, 21-chloro- or 21-acyloxy compounds of general formula I. Polar solvents, preferably dipolar aprotic solvents, such as dimethylformamide, dimethylacetamide, hexamethylphosphorotriamide or N-methylpyrrolidone, to which a small amount of a protic solvent, such as methanol, ethanol or water may be added, are suitable for these reactions. To carry out process variant (e) by use of alkali acylates as the reactant, it is useful to employ the free acid corresponding to the alkali acylate as the solvent for the reaction. The 21-bromo or 21-iodo compounds of general formula VI, moreover, can be converted into the corresponding 21-fluoro- or 21-acyloxycompounds by reaction with silver fluoride or silver acylates (as for example, silver acetate). The 21-monophosphate ester of general formula I can be prepared, for example, by this method by heating the corresponding iodo compound of general formula VI with phosphoric acid in the presence of an organic base, such as triethylamine.

The process according to process variant (f) is accomplished under the same conditions, which one ordinarily applies for the addition of a methyl group to the $\Delta^{16}$-double bond of pregnane-20-one derivatives. Thus one can treat, for example, the compound of formula VII with a methylmagnesium halide, preferably in the presence of copper-(I)-chloride, or lithium dimethylcopper and obtain, after the usual decomposition of the Grignard complex, for example, with mineral acid, D-homosteroids of general formula I having a 17α-bound methyl group and a 17aα-bound hydrogen atom.

On the other hand, treatment of the Grignard complex with acyl halides (preferably acetyl chloride), epoxidation of the reaction mixture with peracid and decomposition of the resulting reaction mixture with mineral acid affords D-homosteroids of general formula I, having a 17α-bound methyl group and a 17aα-bound hydroxy group.

The ketal group bound to the 3-position is cleaved and concurrently, the existing $\Delta^5$-double bond of the molecule is isomerized when one carries out the work up of the reaction mixture in acid medium.

The dehydrogenation of $\Delta^4$-D-homosteroids of general formula I saturated in the 1,2-position can be performed by means of microbiological methods as well as pure chemical methods. For example, the $\Delta^4$-steroids can be dehydrogenated in the 1,2-position with bacteria cultures of the genus Bacillus (for example, *Bacillus lentus* or *Bacillus sphaericus*) or Arthrobacter (for example, *Arthrobacter simplex*) under the usual conditions. Alternatively, it is possible to carry out the $\Delta^1$-dehydrogenation by methods for oxidizing $\Delta^4$-steroids, as for example, by heating with selenium dioxide or 2,3-dichloro-5,6-dicyanobenzoquinone in an inert solvent.

The saponification of the acyl groups situated at the 17,17a- and/or 21-position is effected by means of the usual processes, as for example, by treatment of aqueous, alcoholic or aqueous-alcoholic solutions of the ester with strong acids, as for example, sulfuric acid, hydrochloric acid, p-toluenesulfonic acid or trifluoroacetic acid, or by treatment of the ester in aqueous, alcoholic or aqueous alcoholic solution with alkali metal alkoxides, alkali metal hydroxides or alkali metal carbonates.

It is possible to perform the saponification under mild conditions to selectively saponify the 17aα,21-diacyloxy-D-homosteroids of general formula I to 21-hydroxy-17α-acyloxy-D-homosteroids.

If desired, the 17,17a-situated ketal group can be hydrolized by, for example, treatment of these compounds with acid in aqueous solution or water containing mixed solvents.

The esterification of free hydroxyl groups in the 17,17a- and/or 21-position also takes place by means of known methods. For example, one can esterify the hydroxysteroids with acyl chlorides or acyl anhydrides in the presence of acid, such as, for example, hydrogen chloride, p-toluenesulfonic acid or trifluoroacetic acid, or in the presence of base, such as potassium carbonate, pyridine, collidine or p-dimethylaminopyridine. It is also possible to esterify the hydroxy compounds with carboxylic acids in the presence of trifluoroacetic anhydride. As is known, only the primary and secondary hydroxyl groups are esterified whereas existing tertiary hydroxyl groups if present are not transformed, when the esterification is performed under mild conditions. To selectively esterify only the 21-hydroxyl group of 17,17a,21-trihydroxysteroids, the reaction is advantageously carried out by reacting the trihydroxy compounds with the corresponding acyl anhydrides in the presence of lead acetate.

The alkali sulfate of the 21-monosulfuric acid ester can be prepared from the 21-hydroxy compounds of general formula I by, for example, treatment of the 21-hydroxy compounds with sulfur trioxide in pyridine and transformation of the resultant sulfuric acid ester to the alkali salt by treatment with alkali.

If desired, one can condense D-homosteroids of general formula I, if containing 17,17a-diol groups, with carbonyl compounds of general formula $R_5R_6CO$. This reaction is suitably performed by reaction of the diol with an excess of the carbonyl compounds in the presence of a strong acid, as, for example, hydrochloric acid or perchloric acid or p-toluenesulfonic acid and by addition of dehydrating agents, as for example, the enol acetates or orthoformates.

It was previously mentioned, that the D-homosteroids of general formula I are valuable intermediates, which, in particular, can be applied for the preparation of anti-inflammatory D-homosteroids of general formula VIII

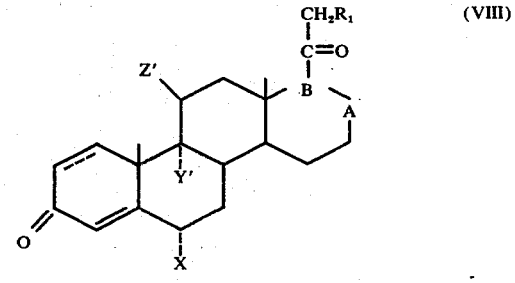

wherein ≕, X, —A—B< and $R_1$ have the same meaning as in formula I and Y' represents a hydrogen atom or fluorine atom and Z' a hydroxy group or Y' represents a chlorine atom and Z' a hydroxy group, a fluorine atom or a chlorine atom. For example, this can be accomplished by 11β-hydroxylation of compounds of general formula I wherein Y and Z are hydrogen by means of methods already described, or by additon of hypochlorous acid to D-homosteroids wherein Y and Z represent a carbon to carbon double bond, for example, by reaction of these compounds with aqueous perchloric acid and N-bromosuccinimide.

Further, one can react the 9,11-epoxide of general formula I with hydrogen fluoride or hydrogen chloride and obtain the corresponding 11β-hydroxy-9α-chloro or 11β-hydroxy-9α-fluorosteroids of general formula VIII.

Moreover, the compounds of general formula I wherein X and Y are hydrogen are especially active pharmacologically and show a spectrum of activity to the corresponding known structurally analogus steroids, which have a five membered D-ring in the steroid framework.

The compounds of the present invention have, however, the advantage, that they are metabolized in the body in a different way than the known steroids, so that they often show a favorable separation between desirable effects and undesirable side effects.

For pharmaceutical effectiveness, the D-homosteroids of general formula I can be formulated in the usual way into medicinal specialties, in which the active material is transformed into the desired dosage forms, such as, tablets, dragees, capsules, solutions, salves and the like.

The starting compounds of general formula II to VII of the processes of this invention were prepared according to methods, which are generally known to those skilled in the art, and, which are further illustrated in the typical examples represented in the following experimentals.

The following examples serve to illustrate the present invention.

EXAMPLES

All temperatures given in degrees centigrade.

EXAMPLE 1

Preparation of 11β,21-Dihydroxy-17α-methyl-D-homo-4-pregnene-3,20-dione.

a. To 45 g of magnesium turnings in 1400 ml of absolute ether was added dropwise 130 ml of methyl iodide. After the magnesium had dissolved 2500 ml of absolute tetrahydrofuran was added and the solution was distilled until the boiling point of the distillate had reached 55°. The mixture was cooled to about 20°, copper-(I)-chloride (7 g) and a solution of 100 g 3β-acetoxy-D-homo-pregna-5,17(17a)-diene-20-one in 1000 ml absolute tetrahydrofuran was added and the mixture was stirred at 20° for 40 minutes. The mixture was then cooled to about 0°. 230 ml of 2-N-sulfuric acid was added dropwise to the mixture and it was then extracted with ethyl acetate. The extract was washed with sodium thiosulfate solution and water, dried over sodium sulfate and concentrated in vacuum. The resulting residue was treated with 300 ml of pyridine and 150 ml of acetic anhydride with warming and the solution so obtained was allowed to stand at room temperature for 16 hours. The mixture was then poured into ice water and the precipitated product was collected by filtration and dissolved in methylene chloride. The methylene chloride solution was washed with dilute sulfuric acid and water, concentrated under vacuum and the residue was recrystallized from methylene chloride-ethyl acetate to obtain 75.6 g of 3β-acetoxy- 17α-methyl-D-homo-5-pregnene-20-one, mp 212°–213°.

b. 3β-Acetoxy-17α-methyl-D-homo-5-pregnene-20-one (30 g) was treated with 300 ml of acetic acid and heated to about 40°–45°. A solution of 7.9 ml of bromine in 60 ml of acetic acid was added dropwise to the mixture over 10 minutes. The reaction mixture was cooled, poured into ice-cold potassium acetate solution and the precipitated product was collected, dissolved in ethyl acetate, the ethyl acetate phase was washed with water and evaporated to dryness at 40° bath temperature under vacuum to obtain the 5,6 21-tribromo-3β-acetoxy-17α-methyl-D-homo-pregnane-20-one as a crude product.

c. The crude product so obtained was treated with 80 g of sodium iodide and 800 ml of acetone and stirred for 16 hours at 20° in the dark. The reaction mixture was then treated with ice-cold sodium thiosulfate solution. The precipitated iodide was collected by filtration, dissolved in ethyl acetate and the ethyl acetate phase was washed with water and evaporated under vacuum.

d. The residue so obtained was dissolved in 420 ml of dimethylformamide, treated with 24 ml of acetic acid and 42 ml of triethylamine and stirred under nitrogen at 120° for 4½ hours. The reaction mixture was then cooled to room temperature, poured into ice-cold sodium chloride solution and the precipitated product was filtered and dissolved in methylene chloride. The methylene chloride solution was washed with water, dried over sodium sulfate, concentrated under vacuum and the residue was purified by chromatography on a silica gel. 3β,21-Diacetoxy-17α-methyl-D-homo-5-pregnene-20-one (19.5 g) which melts at 135.5°–137.5° after recrystallization from ether-pentane was obtained.

e. 3β,21-Diacetoxy-17α-methyl-D-homo-5-pregnene-20-one (24.4 g) was dissolved into 250 ml of methylene chlorine and treated with 250 ml of 1% methanolic potassium hydroxide solution and heated 25 minutes under reflux. 3 ml of acetic acid was added to the reaction mixture. The reaction mixture was evaporated under vacuum. The residue was taken up in tetrahydrofuran and the resulting solution was evaporated under vacuum. The residue was recrystallized from acetone to obtain 15.8 g of 3β,21-dihydroxy-17α-methyl-D-homo-5-pregnene-20-one, mp 198°–202°.

f. 3β,21-Dihydroxy-17α-methyl-D-homo-5-pregnene-20-one (11.7 g) was treated with 150 ml of dimethylformamide, 20 ml of acetic anhydride and 1.1 g of lead diacetate and stirred at room temperature for 90 minutes. The mixture was poured into ice-cold sodium chloride solution. The precipitated product was collected and dissolved in methylene chloride. The methylene chloride extract was washed with water, dried and concentrated under vacuum. The product so obtained was recrystallized from methylene chloride-diisopropyl ether to afford 11.6 g of 3β-hydroxy-21-acetoxy-17α-methyl-D-homo-5-pregnene-20-one, mp 188.5°–191°.

g. 3β-Hydroxy-21-acetoxy-21-acetoxy-17α-methyl-D-homo-5-pregnene-20-one (20.5 g) was treated with 500 ml of toluene and 20 ml of cyclohexanone and was heated to boiling until several ml was distilled. A solution of 4.4 g aluminum isopropylate in 50 ml of toluene was added to the mixture and the mixture was heated an additional hour so that some of the solvent continuously distilled..

The reaction mixture was cooled, diluted with ethyl acetate and the ethyl acetate phase was washed with 1-N-sulfuric acid and water and concentrated under vacuum. The residue was purified by chromatography on silica gel and recrystallized from acetone-hexane to obtain 15.7 g 21-acetoxy-17α-methyl-D-homo-4-pregnene-3,20-dione, mp 200.5°–202°.

h. A 2 1-Erlenmeyer flask containing 500 ml of a nutrient solution of 1% corn steep liquor, 1% soybean powder, .005% soybean oil sterilized in an autoclave at 120° for 30 minutes and standardized to pH 6.2 was inoculated with a lyophilized culture of Curvularia lunata (NRRL 2380) and was shaken for 72 hours at 30° on a rotating shaker. 15 liters of a medium of 1% corn steep liquor, 0.5% d-glucose and 0.005% soybean oil sterilized at 121° and 1.1 atmospheres and standardized to a pH of 6.2 contained in a 20 1 rust-free steel fermenter was inoculated with this preliminary culture. After addition of silicone SH as an antifoam agent the medium was germinated with aeration (10 l/min., 0.7 atmospheres pressure) with stirring (220 revolutions/min.) for 24 hours. 1 liter of the culture broth was transferred under sterile conditions into 14 l. of a medium of 1% corn steep liquor, 1.25% soybean powder and 0.005% soybean oil sterilized as above and was cultured under the same conditions. After 6 hours a solution of 3 g 21-acetoxy-17α-methyl-D-homo-4-pregnene-3,20-dione in 150 ml of dimethyl formamide was added. After 23 hours contact time the contents of the fermenter was stirred 2 times each with 10 l of methylisobutylketone and the extract was evaporated under vacuum at a bath temperature of 50°. To remove the silicone oil the residue was washed several times with hexane and recrystallized from ethyl acetate to which activated charcoal was added, whereby 608 mg of pure 11β,21-dihydroxy-17α-methyl-D-homo-4-pregnene-3,20-dione, mp 200.3° was obtained.

EXAMPLE 2

Preparation of
11β,21-Dihydroxy-17α-methyl-D-homo-1,4-pregnadiene-3,20-dione.

500 ml of a nutrient solution of 1.5% peptone, 1.2% corn steep and 0.2% magnesium sulfate sterilized in an autoclave at 120° for 30 minutes, adjusted to a pH of 6.5 and contained in a 2 1-Erlenmeyer flask was inoculated with a lyophilized culture of Bacillus lentus (ATCC 13 805) and was shaken for 24 hours at 30°. 15 l of a fluid nutrient medium of 0.2% yeast extract, 1% corn steep liquor and 0.1% d-glucose sterilized at 121° and 1.1 atmospheres, standardized to pH 7.0 and contained in a rust-free steel fermenter was inoculated with this preliminary culture. After addition of silicone SH as an antifoam agent, the broth was germinated at 29° with aeration and stirring. After a growth phase of 6 hours a solution of 3 g of 11β,21-dihydroxy-17α-methyl-D-homo-4-pregnene-3,20-dione in 150 ml of dimethylformamide was added.

After 15 hours of contact time the contents of the fermenter were extracted 2 times each with 10 l of methyl isobutyl ketone and the extract was evaporated under vacuum. To remove the silicone oil the residue was washed with hexane and recrystallized from acetone-diisopropyl ether in the presence of activated charcoal to obtain 2.2 g of 11β,21-dihydroxy-17α-methyl-D-homo-1,4-pregnadiene-3,20-dione, mp 159°.

EXAMPLE 3

Preparation of
11β-Hydroxy-21-butyryloxy-17α-methyl-D-homo-1,4-pregnadiene-3,20-dione.

11β,21-Dihydroxy-17α-methyl-D-homo-1,4-pregnadiene-3,20-dione (200 mg) was treated with 3 ml of pyridine and 0.3 ml butyric acid anhydride and heated under reflux for 15 minutes. The mixture was cooled, diluted with cyclohexane and evaporated under vacuum. The oily residue was triturated with pentane, the pentane solution was decanted and the crude product so obtained was recrystallized from methylene chloride-diisopropyl ether to obtain 140 mg of 11β-hydroxy-21-butyryloxy-17α-methyl-D-homo-1,4-pregnadiene-3,20-dione, mp 156°–158°.

EXAMPLE 4

Preparation of
11β-Hydroxy-21-acetoxy-17α-methyl-D-homo-1,4-pregnadiene-3,20-dione.

11β,21-Dihydroxy-17α-methyl-D-homo-1,4-pregnadiene-3,20-dione (5.0 g) was treated with 20 ml of pyridine and 10 ml of acetic anhydride and was kept at room temperture for 60 minutes. The reaction mixture was poured into ice water and the precipitated product was collected by filtration, dissolved in methylene chloride, and the methylene chloride phase was washed with 2-N- sulfuric acid and water and evaporated under vacuum. The residue was recrystallized from methylene chloride-diisopropyl ether to obtain 5.1 g of 11β-hydroxy-21-acetoxy-17α-methyl-D-homo-1,4-pregnadiene-3,20-dione, mp 170°–172°.

EXAMPLE 5

Preparation of
9α-Fluoro-11β-hydroxy-21-acetoxy-17α-methyl-D-homo-1,4-pregnadiene-3,20-dione.

a. 11β-Hydroxy-21-acetoxy-17α-methyl-D-homo-1,4-pregnadiene-3,20-dione (50 g) was dissolved in 44 ml of pyridine and 22 ml of methanesulfonyl chloride was added dropwise with stirring. The reaction mixture was heated for 90 minutes at 80°, allowed to cool and poured into ice water. The precipitated product was collected by filtration, washed with water, dried under vacuum and recrystallized from methylene chloride-diisopropyl ether to obtain 39.2 g of 21-acetoxy-17α-methyl-D-homo-1,4,9(11)-pregnatriene-3,20-dione, mp 161°–163°.

b. 21-Acetoxy-17α-methyl-D-homo-1,4,9(11)-pregnatriene-3,20 -dione (11 g) was suspeneded in 200 ml of tetrahydrofuran and was treated with 88 ml of 1-N-perchloric acid. N-bromosuccinimide (14.3 g) was added to the reaction mixture with stirring and the reaction mixture was stirred at 30° for 30 minutes. The mixture was poured into ice-cold sodium sulfite solution. The precipitated product was collected by filtration and was taken up in methylene chloride. The methylene chloride phase was washed with water and evaporated under vacuum to obtain 9α-bromo-11β-hydroxy- 21-acetoxy-17α-methyl-D-homo-1,4-pregnadiene-3,20-dione as the crude product.

c. The bromohydrin (13.6 g) so obtained was treated with 22 g of potassium acetate and 100 ml of ethanol and was heated under reflux for 2 hours. The reaction mixture was poured into water and the precipitate was collected by filtration, dried under vacuum to obtain 9β,11β-epoxy-21-acetoxy-17α-methyl-D-homo-1,4-pregnadiene-3,20-dione as the crude product.

d. The resulting crude product (8.0 g) was added to a mixture of 24 ml of dimethylformamide and 35 ml of hydrogen fluoride, cooled to −10° and the mixture was stirred at room temperature for 10 hours. The mixture was poured into ammonia containing ice water and the precipitated product was collected by filtration, dissolved in methylene chloride and the methylene chloride phase was washed with water and concentrated under vacuum. The residue was recrystallized from acetone-hexane to obtain 5.8 g 9α-fluoro-11β-hydroxy-21-acetoxy-17α-methyl-D-homo-1,4-pregnadiene-3,20-dione, mp 183°–185°.

EXAMPLE 6

Preparation of
9α-Fluoro-11β,21-hydroxy-17α-methyl-D-homo-1,4-pregnadiene-3,20-dione.

9α-Fluoro-11β-hydroxy-21-acetoxy-17α-methyl-D-homo-1,4-pregnadiene-3,20-dione (3 g) was treated with 12 ml of methanol and 12 ml of methylene chloride, cooled to −5° and a solution of 0.18 g of potassium hydroxide in 6 ml of methanol was added dropwise. The mixture was then stirred for 60 minutes at 0°, neutralized with acetic acid, diluted with methylene chloride and the methylene chloride phase was washed with water and concentrated under vacuum. Recrystallization of the residue from methanol afforded 2.4 g of 9α-fluoro-11β,21-dihydroxy-17α-methyl-D-homo-1,4-pregnadiene-3,20-dione, mp 223°–225°.

EXAMPLE 7

Preparation of
Sodium-[9α-fluoro-11β-hydroxy-3,20-dioxo-17α-methyl-D-homo-1,4-pregnadiene-21-yl] sulfate.

Pyridine (4 ml) was cooled to −15° and was treated with 0.26 ml of freshly distilled sulfurtrioxide with stirring so that the internal temperature of the mixture did not exceed +5°. 9α-Fluoro-11β,21-dihydroxy-17α-methyl-D-homo-1,4-pregnadiene-3,20-dione (2 g) was added to the so obtained solution and the mixture was stirred at 20° for 30 minutes and then treated with 40 ml of water and stirred for an additional 30 minutes. 7 ml of 1-N-sodium hydroxide solution was added to the reaction mixture until a pH value of 8.5 is reached. The mixture was extracted with methylene chloride and the aqueous phase was evaporated under vacuum after adjustment of the pH to 8.5 with 1-N-sodium hydroxide solution. The residue was dissolved in 50 ml of methanol, filtered and the filtrate was concentrated under vacuum. The residue was dried under vacuum to give 1.8 g of sodium-[9α-fluoro- 11β-hydroxy-3,20-dioxo-17α-methyl-D-homo-1,4-pregnadiene-21-yl] sulfate, decomposition point 191°.

EXAMPLE 8

Preparation of
6α-Fluoro-11β,21-dihyroxy-17α-methyl-D-homo-4-pregnene-3,20-dione.

a. A Grignard solution, prepared from 21 g of magnesium turnings, 72.5 g of methyl iodide and 1000 ml of ether was diluted with 1000 ml of absolute tetrahydrofuran and was distilled until the distillate had reached a boiling point of 50°. The obtained suspension was treated with 4 g of copper-(I)-chloride and a solution of 50 g of 3β-hydroxy-D-homo-5,17(17a)-pregnadiene-20-one in 2000 ml of absolute tetrahydrofuran at 20° and the mixture was stirred at room temperature for 20 minutes. The reaction mixture was worked up in the usual way and the crude product was recrystallized for acetone to obtain 32.5 g of 3β-hydroxy-17α-methyl-D-homo-5-pregnene-20-one, mp 207°–209°.

b. 3β-Hydroxy-17α-methyl-D-homo-5-pregnene-20-one (10 g) was suspended in 1000 ml of tetrahydrofuran and was treated dropwise with a solution of 3.6 ml of bromine in 10 ml of acetic acid over a period of about 15 minutes. The reaction mixture was worked up as described in Example 1 (b) to obtain 3β-hydroxy-5,6,21-tribomo-17α-methyl-D-homo-pregnane-20-one as the crude product.

c. The so obtained tribromo derivative was transformed by sodium iodide (35 g) and acetone (300 ml) under the conditions described in Example 1 (c) and worked up by the method described in Example 1 (c) to give the 21-iodo compound as the crude product.

d. The 21-iodide was dissolved in 140 ml of dimethylformamide and was treated with 8 ml of acetic acid and 41 ml of triethylamine and stirred at 90° for 11 hours. The reaction mixture was worked up as described in Example 1 (d) to obtain 4.4 g of 3β-hydroxy-21-acetoxy-17α-methyl-D-homo-5-pregnene-20-one which melts at 188°–190° after recrystallization from methylene chloride-diisopropyl ether.

e. To a solution of 3 ml of hydrogen fluoride and 3 ml of dimethylformamide, N-bromosuccinimide (470 mg) was added at 30°. A previously cooled solution of 1 g of 3β-hydroxy-21-acetoxy-17α-methyl-D-homo-5-pregnene-20-one in an 8 ml of methylene chloride was added portionwise to the mixture. The mixture was stirred for 10 minutes at −30° and was then poured into ice-cold potassium hydrogen carbonate solution and extracted with methylene chloride. The methylene chloride phase was washed with water and evaporated to dryness under vacuum and the residue was recrystallized from acetone to give 627 mg of 6β-fluoro-5α-bromo-3β-hydroxy-21-acetoxy-17α-methyl-D-homo-5α-pregnane-20-one, mp 168.5° (decomposition).

f. 6β-Fluoro-5α-bromo-3β-hydroxy-21-acetoxy-17α-methyl-D-homo-5α-pregnane-20-one (300 mg) in 10 ml of acetone was treated dropwise with 0.19 ml of Jones reagent (containing 267 g of chromic acid, 230 ml of concentrated sulfuric cid per liter of water) and the mixture was stirred at 20° for 10 minutes. The mixture was poured into ice water. The precipitate was collected by filtration and was taken up in methylene chloride and the methylene chloride phase was washed with water and evaporated under vacuum to obtain 298 mg of 6β-fluoro-5α-bromo-21-acetoxy-17α-methyl-D-homo-5α-pregnane-3,20-dione as the crude product.

g. This crude product was dissolved in 5 ml of acetic acid and stirred at 30° for 3 hours. The mixture was treated with 100 mg of sodium acetate, stirred for 10 minutes at 30°, poured into ice water and the precipitate was collected by filtration and taken up in methylene chloride. The methylene chloride phase was washed with water and evaporated under vacuum. The residue was recrystallized from acetone to yield 250 mg of 6α-fluoro-21-acetoxy-17α-methyl-D-homo-4-pregnene-3,20-dione.

h. 6α-Fluoro-21-acetoxy-17α-methyl-D-homo-4-pregnene-3,20-dione (3 g) was fermented with Curvularia lunata and worked up under the conditions described in Example 1 (h) to give 6α-fluoro-11β,21-dihydroxy-17α-methyl-D-homo-4-pregnene-3,20-dione.

EXAMPLE 9

Preparation of 6α-Fluoro-11β,21-dihydroxy-17α-methyl-D-homo-1,4-pregnadiene-3,20-dione.

6α-Fluoro-11β,21-dihydroxy-17α-methyl-D-homo-4-pregnene-3,20-dione (1.2 g) was transformed with a culture of Bacillus lentus and worked up according to the conditions described in Example 2 to give 6α-fluoro-11β,21-dihydroxy-17α-methyl-D-homo-1,4-pregnadiene-3,20-dione.

EXAMPLE 10

Preparation of 6α-Fluoro-11β-hydroxy-21-acetoxy-17α-methyl-D-homo-1,4-pregnadiene-3,20-dione.

6α-Flouro-11β,21-dihydroxy-17α-methyl-D-homo-1,4-pregnadiene-3,20-dione (10 g) in 40 ml of pyridine was treated with 20 ml of acetic anhydride and stirred at room temperature for 90 minutes. The reaction mixture was worked up as described in Example 3 to obtain 9.5 g of 6α-fluoro-11β-hydroxy-21-acetoxy-17α-methyl-D-homo-1,4-pregnadiene-3,20-dione, mp 213°–215°.

EXAMPLE 11

Preparation of 6α-Fluoro-9α-chloro-11β-hydroxy-21-trimethylacetoxy-17α-methyl-D-homo-1,4-pregnadiene-3,20-dione.

a. 6α-Fluoro-11β,21-dihydroxy-17α-methyl-D-homo-1,4-pregnadiene-3,20-dione (5 g) was treated with 15 ml of pyridine and 5 ml of trimethylacetic acid anhydride and heated under reflux for 6 hours. The reaction mixture was diluted with 30 ml of pyridine, cooled to 50° and 2 ml of thionyl chloride was added dropwise to the solution and the mixture was stirred at 0° for 30 minutes. The mixture was poured into ice water and the precipitate was collected by filtration, washed with water, dried under vacuum and recrystallized from methylene chloride to give 4.9 g of 6α-fluoro-21-trimethylacetoxy-17α-methyl-D-homo-1,4,9(11)-pregnatriene-3,20-dione, mp 191°–192.5°.

b. 6α-Fluoro-21-trimethylacetoxy-17α-methyl-D-homo-1,4,9(11)-pregnatriene-3,20-dione (380 mg) was dissolved in 15 ml of tetrahydrofuran and treated with 1.2 g of N-chlorosuccinimide and 11 ml of 1-N-aqueous perchloric acid. The mixture was stirred at 35° for 3 hours and was then poured into ice water and extracted with methylene chloride. The methylene chloride phase was washed with water and evaporated under vacuum. The residue was recrystallized from acetone-diisopropyl ether to give 250 mg of 6α-fluoro-9α-chloro-11β-hydroxy-21-trimethylacetoxy-17α-methyl-D-homo-1,4-pregnadiene-3,20-dione, mp 221°–223°.

EXAMPLE 12

Preparation of 6α-Fluoro-9α-chloro-11β-hydroxy-21-acetoxy-17α-methyl-D-homo-1,4-pregnadiene-3,20-dione.

a. 6α-Fluoro-11β-hydroxy-21-acetoxy-17α-methyl-D-homo-1,4-pregnadiene-3,20-dione (500 mg) was treated with 25 ml of dimethylformamide, 4.5 ml of pyridine and 2.2 ml of methanesulfonyl chloride and was heated at 80° for 90 minutes. The reaction mixture was worked up as described in Example 5 (a) to obtain 4.2 mg of 6α-fluoro-21-acetoxy-17α-methyl-D-homo-1,4,9(11)-pregnatriene-3,20-dione, mp 187°–189°.

b. 6α-Fluoro-21-acetoxy-17α-methyl-D-homo-1,4,9(11)-pregnatriene-3,20-dione (375 g) was dissolved in 15 ml of tetrahydrofuran and was treated with 1.2 g of N-chlorosuccinimide and 11 ml of 1-N-aqueous perchloric acid and was stirred at 35° for 3 hours. The reaction mixture was worked up as described in Example 11 (b) to obtain 266 mg of 6α-fluoro-9α-chloro-11β-hydroxy-21-acetoxy-17α-methyl-D-homo-1,4-pregnadiene-3,20-dione, mp 207°–209°.

EXAMPLE 13

Preparation of 6α,9α-Difluoro-11β-hydroxy-21-acetoxy-17α-methyl-D-homo-1,4-pregnadiene-3,20-dione.

a. 6α-Fluoro-11β-hydroxy-21-acetoxy-17α-methyl-D-homo-1,4-pregnadiene-3,20-dione (5.0 g) was treated and worked up under the conditions described in Example 5 (a) to obtain 3.7 g of 6α-fluoro-21-acetoxy-17α-methyl-D-homo-1,4,9(11)-pregnatriene-3,20-dione, mp 173°–175°.

b. The pregnatriene compound so obtained was converted to 6α,9α-difluoro-11β-hydroxy-21-acetoxy-17α-methyl-D-homo-1,4-pregnadiene-3,20-dione, mp 199°–201°, under the conditions described in Example 5 (b) to (d).

EXAMPLE 14

Preparation of 6α,9α-Difluoro-11β,21-dihydroxy-17α-methyl-D-homo-1,4-pregnadiene-3,20-dione.

6α,9α-Difluoro-11β-hydroxy-21-acetoxy-17α-methyl-D-homo-1,4-pregnadiene-3,20-dione (3.0 g) was saponified under the conditions described in Example 6 to obtain 2.6 g of 6α,9α-difluoro-11β,21-dihydroxy-17α-methyl-D-homo-1,4-pregnadiene-3,20-dione, mp 190°–191°.

EXAMPLE 15

Preparation of 6α-Fluoro-9α,11β-dichloro-21-acetoxy-17α-methyl-D-homo-1,4-pregnadiene-3,20-dione.

6α-Fluoro-21-acetoxy-17α-methyl-D-homo-1,4,9(11)-pregnatriene-3,20-dione (1.0 g) was dissolved in 50 ml of acetic acid, cooled to 0° and treated with 4 g of lithium chloride. To the mixture, 400 mg of N-chlorosuccinimide and a solution of 110 mg of hydrogen chloride in 1 ml of tetrahydrofuran was added and the mixture was stirred at room temperature for 5 hours and poured into ice water. The precipitated product was collected by filtration, taken up in methylene chloride and the methylene chloride phase was washed with water and concentrated under vacuum. The residue was recrystallized from ether-pentane to obtain 590 mg of 6α-fluoro-9α,11β-dichloro-21-acetoxy-17α-methyl-D-homo-1,4-pregnadiene-3,20-dione, mp 232°–234°.

EXAMPLE 16

Preparation of 6α,11β-Difluoro-9α-chloro-21-acetoxy-17α-methyl-D-homo-1,4-pregnadiene-3,20-dione.

A mixture of 4.2 ml of hydrogen fluoride, 5.7 ml of tetrahydrofuran and 8 ml of methylene chloride was cooled to −70° and was treated with 2.0 g of 6α-fluoro-21-acetoxy-17α-methyl-1,4,9(11)-pregnatriene-3,20-dione and 1.0 g of N-chlorosuccinimide and stirred at −60° for 5 hours. An additional 2 g of N-chlorosuccinimide was added to the mixture and the mixture was allowed to stand at 0° for 15 hours. The reaction mixture was added to ice-cold potassium hydrogen carbonate solution and was extracted with methylene chlorine. The methylene chloride phase was washed with sodium sulfate solution and water and evaporated under vacuum. The residue was recrystallized from acetone-hexane to obtain 1.3 g of 6α,11β-difluoro-9α-chloro-21-acetoxy-17α-methyl-D-homo-1,4-pregnadiene-3,20-dione, mp 244°–246°.

EXAMPLE 17

Preparation of Di-sodium-(6α-fluoro-11β-hydroxy-3,20-dioxo-17α-methyl-D-homo-1,4-pregnadiene-21-yl)-phosphate.

To a solution of 20 g of 6α-fluoro-11β,21-dihydroxy-17α-methyl-D-homo-1,4-pregnadiene-3,20-dione in 200 ml of pyridine, 20 ml of methanesulfonyl chloride was added dropwise with cooling and stirring. After a reaction time of 30 minutes, the reaction mixture was poured into ice water and the precipitated 21-mesylate was collected by filtration. 6α-Fluoro-11β-hydroxy-21-mesyloxy-17α-methyl-D-homo-1,4-pregnadiene-3,20-dione (15.4 g) was dissolved in 500 ml of acetone, after the addition of 15.4 g of sodium iodide in 400 ml of acetone was heated at boiling for 15 minutes. The filtered reaction mixture was evaporated under vacuum; the residue was stirred with dilute sodium thiosulfate solution, collected on filter, washed with water, dissolved in 300 ml of acetone and precipitated with 120 ml of water with warming. 6α-Fluoro-21-iodo-11β-hydroxy-17α-methyl-D-homo-1,4-pregnadiene-3,20-dione (14.1 g) was isolated upon cooling. 14.1 g of the 21-iodo compound was dissolved in 700 ml of acetonitrile and was heated under reflux for 3 hours with 14.1 g of orthophosphoric acid and 42 ml of triethylamine. The reaction mixture was then evaporated under reduced pressure. The residue was taken up in methanol and the solution was adjusted to a pH of 11 with 1-N-methanolic sodium hydroxide. The residue was filtered and the filtrate was concentrated under vacuum. The residue was taken up in 70 ml of methanol. The disodium salt precipitated upon the addition of ether. The disodium salt can be purified by precipitation by ether from methanol. Disodium (6α-fluoro-11β-hydroxy-3,20-dioxo-17α-methyl-D-homo-1,4-pregnadiene-21-yl)-phosphate (11.9 g) was obtained.

EXAMPLE 18

Preparation of 6α-Fluoro-11β,21-dihydroxy-D-homo-4-pregnene-3,20-dione.

6α-Fluoro-21-acetoxy-D-homo-4-pregnene-3,20-dione, mp 178°–180°, was obtained from 3β-hydroxy-21-acetoxy-D-homo-5-pregnene-20-one under the conditions described in Examples 8 (e), (f) and 9, and can be transformed under the conditions described in Example 1 (h) to 6α-fluoro-11β,21-dihydroxy-D-homo-4-pregnene-3,20-dione.

EXAMPLE 19

Preparation of
11β,21-Dihydroxy-17α-methyl-D-homo-4-pregnene-3,20-dione.

a. An Erlenmeyer flask containing 500 ml of a sterilized aqueous medium containing 0.3% yeast extract, 0.5% corn steep liquor and 0.2% starch standardized to pH 7 was inoculated with a lyophilized culture of Flavobacterium dehydrogenans (ATCC 13930) and was shaken for 48 hours at 30° and 145 revolutions per minute. A 20 l fermenter charged with 14.75 l of a sterilized nutrient solution of the same composition was inoculated with 250 ml of the bacterium suspension and was stirred for 24 hours at 29° with aeration of 1650 l/hr at 220 revolutions per minute. suspension 0.9 l of the preliminary fermentation was transferred to a 20 l fermenter which was charged with 15 l of the sterilized medium of the same composition. The same conditions were applied to the main fermentation as those applied to the preliminary fermentation; thereby the pH value was maintained between 6 to 7 diacetoxy-17α-methyl-D-homo-5-pregnene-20-one in 60 ml of dimethylformamide was added to the broth and was fermented.

After 32 hours of contact time the fermentation mixture was extracted two times each with 15 l of methyl isobutyl ketone and the organic phase was evaporated. The residue was taken up in methylene chloride and the methylene chloride phase was filtered through silica gel and evaporated under vacuum to obtain 2.7 g of 21-hydroxy-17α-methyl-D-homo-4-pregnene-3,20-dione as the crude product.

b. The so obtained 21-hydroxy-17α-methyl-D-homo-4-pregnene-3,20-dione, without further purification, was fermented with Curvularia lunata under the conditions described in Example 1h to obtain after the usual work up 480 mg of 11β,21-dihydroxy-17α-methyl-D-homo-4-pregnene-3,20-dione, mp 198°–199.5°.

EXAMPLE 20

Preparation of
6α-Fluoro-11β-hydroxy-21-acetoxy-17α-methyl-D-homo-4-pregnene-3,20-dione.

a. 6α-Fluoro-21-acetoxy-17α-methyl-D-homo-4-pregnene-3,20-dione (3.0 g) was fermented with Aspergillus ochraceus (ATTC 1008) under the conditions described in Example 1 (h). After completion of the fermentation, the fermentation mixture was extracted with methyl isobutyl ketone and the methyl isobutyl ketone extract was evaporated under vacuum to obtain 6α-fluoro-11α,21-dihydroxy-17α-methyl-D-homo-4-pregnene-3,20-dione as the crude product.

b. The so obtained crude product was fermented with Bacillus lentus under the conditions described in Example 2. The reaction mixture was worked up in the usual way to obtain 890 mg of 6α-fluoro-11α,21-dihydroxy-17α-methyl-D-homo-1,4-pregnadiene-3,20-dione.

c. 6α-Fluoro-11α,21-dihydroxy-17α-methyl-D-homo-1,4-pregnadiene-3,20-dione (750 mg) in 10 ml of dimethylformamide was treated with 2 ml of acetic anhydride and 0.2 g of lead diacetate and was stirred at room temperature for 60 minutes.

The reaction mixture was then diluted with methylene chloride and the methylene chloride phase was washed with water and evaporated to dryness.

d. The so obtained crude 6α-fluoro-11α-hydroxy-21-acetoxy-17α-methyl-D-homo-1,4-pregnadiene-3,20-dione was kept with 7 ml of pyridine and 0.8 ml of methanesulfonyl chloride for 3 hours at 0°. The reaction mixture was poured into ice water, extracted with water washed methylene chloride and the methylene chloride phase was evaporated under vacuum. The residue so obtained was dissolved in 10 ml of dimethylformamide, treated with 0.8 g of lithium chloride and the mixture was heated at 100° for 90 minutes. The mixture was then poured into ice water, extracted with methylene chloride and the methylene chloride phase was washed with water and evaporated under vacuum. The crude product so obtained was purified by chromatography on a silica gel column and recrystallized from methylene chloride-diisopropyl ether to obtain 210 mg of 6α-fluoro-21-acetoxy-17α-methyl-D-homo-1,4,9(11)-pregnatriene-3,20-dione, mp 186°–188°.

e. 6α-Fluoro-21-acetoxy-17α-methyl-D-homo-1,4,9(11)-pregnatriene-3,20-dione (200 mg) was transformed under the conditions described in Example 5 (b) to 6α-fluoro-9α-bromo-11β-hydroxy-21-acetoxy-17α-methyl-D-homo-1,4-pregnadiene-3,20-dione (180 mg) as the crude product.

f. The so obtained bromohydride was dissolved in 4 ml of tetrahydrofuran, treated with 1.2 ml of tributyl tin hydride and was warmed for 90 minutes at 80°. To the mixture was added 1 mg of azodiisobutyronitrile and the mixture was warmed an additional 30 minutes. The reaction mixture was poured into ice water, extracted with methylene chloride and the methylene chloride phase was washed with 1-N-sulfuric acid, sodium hydrogen carbonate solution and water and concentrated under vacuum to give 110 mg of 6α-fluoro-11β-hydroxy-21-acetoxy-17α-methyl-D-homo-4-pregnene-3,20-dione.

EXAMPLE 21

Preparation of
11β,17α,17aα,21-tetrahydroxy-D-homo-4-pregnene-3,20-dione.

a. 3β-Acetoxy-D-homo-5,17-pregnadiene-20-one (5.6 g) was treated with 350 ml of tetrahydrofuran and 6.8 g of copper-(II)-bromide and was heated under reflux for 4 hours. The reaction mixture was poured into ice water, extracted with methylene chloride and the methylene chloride phase was washed and evaporated under vacuum to obtain crude 21-bromo-3β-acetoxy-D-homo-5,17-pregnadiene-20-one, which after recrystallization from ether-hexane melts at 155°–157°.

b. The bromide was converted under the conditions described in Example 1 (d) to 3β,21-diacetoxy-D-homo-5,17-pregnadiene-20-one (mp 133°–134°) after the usual work up.

c. The diacetate, so obtained, was saponified according to the conditions described in Example 1 (e) to afford 3β,21-dihydroxy-D-homo-5,17-pregnadiene-20-one.

d. The dihydroxy compound was esterified according to conditions given in Example 1 (f) to give 3β-hydroxy-21-acetoxy-D-homo-5,17-pregnadiene-20-one, mp 201°–202°.

e. A solution of 5.7 g of 3β-hydroxy-21-acetoxy-D-homo-5,17-pregnadiene-20-one and 170 ml of toluene was treated with 80 ml of cyclohexanone and 6.6 g of aluminum tert.-butylate and was heated under reflux for 2 hours on the water bath. The mixture was poured into ice water, acidified with hydrochloric acid and extracted with methylene chloride. The methylene chloride phase was washed with water, dried over sodium sulfate, evaporated under vaccum and the residue was purified by chromatography on a silica gel column to afford 21-acetoxy-D-homo-4,17-pregnadiene-3,20-dione, mp 159°–160°.

f. A solution of 3.0 g of 21-acetoxy-D-homo-4,17-pregnadiene-3,20-dione and 300 ml of benzene and 30 ml of pyridine was treated with a solution of 2.4 g of osmium tetroxide in 60 ml of benzene. The mixture was stirred for 2 hours at room temperature, evaporated under vacuum and the residue in 400 ml of dioxane was added to 80 ml of a 40% sodium hydrogen sulfite solution and the mixture was stirred an additional 30 minutes. The mixture was concentrated under vacuum to one-half of its original volume, and the residual was poured into ice water and extracted with methylene chloride. The methylene chloride phase was washed with sodium carbonate solution and water, dried over sodium sulfate and evaporated under vacuum. The residue was purified over a kiesel gel column to afford 17α,17aα-dihydroxy-21-acetoxy-D-homo-4-pregnene-3,20-dione, mp 230°–232° (from acetone).

g. The 17α,17α-dihydroxy-21-acetoxy-D-homo-4-pregnene-3,20-dione was fermented with *Curvularia lunata* under the conditions described in Example 1 (h) to obtain, after the usual work up 11β,17α,17aα,21-tetrahydroxy-D-homo-4-pregnene-3,20-dione, mp 261°–262°.

EXAMPLE 22

Preparation of
11β,17aα-Dihydroxy-21-acetoxy-17α-methyl-D-homo-4-pregnene-3,20-dione.

a. 3β,11β-Diacetoxy-androsta-3,5-diene-17-one was transformed into 3,11β-acetoxy-17,17-ethylenedioxy-androsta-3,5-diene, mp 183°–186° by ethylene glycol in the presence of methyl orthoformate p-toluene sulfonic acid at room temperature.

The above 17-ketal in tetrahydrofuran-methanol was reduced with sodium borohydride to 11β-acetoxy-17,17-ethylenedioxy-3β-hydroxy-androst-5-en (mp 125°–126°).

Splitting the ketal with aqueous acetone and p-toluene sulfonic acid gave 11β-acetoxy-3β-hydroxy-androst-5-en-17-one, mp 193°–195°. This 17-ketosteroid was converted to 21-Nor-11β-acetoxy-17,20-epoxy-3β-hydroxy-pregn-5-ene, mp 155°–156° by dimethyl sulfoxonium methylide.

The epoxide in alcohol was converted to 11β-acetoxy-17-aminomethyl-3β,17-dihydroxy-androst-5-ene by concentrated ammonia in an autoclave. D-Homo-11β-acetoxy-3β-hydroxy-androst-5-en-17a-one, mp 230°–232°, was obtained therefrom with sodium nitrite in acetic acid and water.

Saponification of the 11β-acetates in boiling methanolic potassium hydroxide gave D-homo-3β,11β-dihydroxy-androst-5-en-17a-one, mp 234°–236°.

3β,11β-Dihydroxy-D-homo-androst-5-en-17a-one was condensed with diethyl oxalate to 3β,11β-dihydroxy-17-ethoxalyl-D-homo-androst-5-en-17a-one.

The above was converted by methyl iodide in acetone in the presence of potassium carbonate to the 17-methyl derivative.

Splitting of the oxalyl residue in methanolic sodium methoxide solution gave 3β,11β-dihydroxy-17α-methyl-D-homo-androst-5-en-17a-one, mp 209°–211°.

The 3β,11β-dihydroxy-17a-methyl-D-homo-5-androsten-17a-one in tetrahydrofuran was transformed by ethinyl magnesium bromide to 3β,11β,17aα-trihydroxy-17β-methyl-17aβ-ethinyl-D-homo-5-androstene, which after treatment with mercury p-toluene sulfonamide in boiling alcohol yields 3β,11β,17aα-trihydroxy-17α-methyl-D-homo-5-pregnene-20-one, mp 212°–214°.

b. 3β,11β,17aα-Trihydroxy-17α-methyl-D-homo-pregn-5-en-20-one (1.7 g) in 10 ml of methanol and 2.1 ml of 10% methanolic calcium chloride solution and 1 g of anhydrous calcium oxide and a solution of 2.32 g of iodine and 600 mg of calcium chloride in 6 ml of methanol was then added dropwise over 30 minutes with continuous stirring. The reaction mixture was stirred an additional 10 minutes, poured into ice water and extracted with methylene chloride. The extract was washed with dilute sodium chloride solution, dried and evaporated to obtain 2.5 g of thin layer chromatographically pure 3β,11β,17aα-trihydroxy-21,21-diiodo-17α-methyl-D-homo-pregn-5-en-20-one, which was further processed without purification.

c. 2.5 g of the above described diiodide in 30 ml of acetone was heated under reflux with 0.3 ml of water, 0.3 ml of acetic acid and 3 g of calcium acetate for 5 days. The mixture was poured into water and extracted with methylene chloride; the methylene chloride solution was washed with dilute sodium chloride solution, dried and evaporated to obtain 1.9 g of almost thin layer chromatographically pure 3β,11β,17aα-trihydroxy-21-acetoxy-17α-methyl-D-homo-pregn-5-en-20-one.

d. The above was converted into 21-acetoxy-11β,17aα-dihydroxy-17α-methyl-D-homo-pregn-4-en-3,20-dione by the same method as described in Example 1 (g). Chromatography of the crude product gave 11β,17aα-dihydroxy-21-acetoxy-17αmethyl-D-homo-4-pregnene-3,20-dione, mp 210°–212° (from ethyl acetate).

EXAMPLE 23

Preparation of
11β,17aα-Dihydroxy-17α-methyl-D-homo-pregn-4-en-3,20-dione.

3β,11β,17aα-Trihydroxy-17α-methyl-D-homo-pregn-5-ene-20-one (2 g) in 20 ml cyclohexanone and 60 ml toluene was heated to boiling. 10 ml of the solution was removed by distillation. Aluminum tri-tert. butoxide (2 g) was added to the mixture cooled to about 5°. The reaction mixture was heated for 1 hour on the water bath. After cooling, the reaction mixture was poured into dilute aqueous acetic acid and extracted with methylene chloride. The methylene chloride solution was washed with water, dried and evaporated. The difficulty volatile part was removed by distillation under high vacuum at a temperature of about 140°. The residue was purified by chromatography to obtain 11β,17aα-dihydroxy-17α-methyl-D-homo-pregn-4-ene-3,20-dione, mp 231°–234°.

EXAMPLE 24

Preparation of
9α-Chloro-11β-hydroxy-17α,17aα-isopropylidene
dioxy-D-homo-4-pregnene-3,20-dione.

a. 3β,11α-Dihydroxy-5-androsten-17-one in dimethylformamide was converted to 3β,11α-dihydroxy-17,20-epoxy-21-nor-5-pregnene, mp 190°–193°, by dimethylsufoxoniummethylide.

The so obtained epoxide was converted to 17-aminomethyl-3β,11α11α,17-trihydroxy-5-androstene, which formed 3β,11α-dihydroxy-D-homo-5-androsten-17a-one mp 200°–201°, by concentrated ammonia in alcohol in an autoclave.

This D-homo compound was treated with potassium acetylide in liquid ammonia to give 3β,11α, 17a-trihydroxy-17a-ethinyl-D-homo-5-androstene, mp 204°–205°.

This ethinyl compound was esterified with acetic anhydride and pyridine at room temperature to obtain 17a-hydroxy-3β,11α-diacetoxy-17a-ethinyl-D-homo-5-androstene, mp 208°–211°.

The so obtained diacetoxy compound was treated with phosphorousoxychloride and 2,4-lutidine at 120° for 20 hours to obtain 3β,11α-diacetoxy-17a-ethinyl-D-homo-5,17-androstadiene as a colorless oil.

The androstadiene was converted to 3β,11α-diacetoxy-D-homo-5,17-pregnadiene-20-one, mp 216°–217°. The diacetate, so obtained, was treated with sodium carbonate in methanol to obtain 3β-hydroxy-11α-acetoxy-D-homo-5,17-pregnadiene-20-one, mp 220°–222°, which gave 11α-acetoxy-D-home-4,17-pregnadiene-3,20-dione, mp 147°–148°, by Oppenauer oxidation.

The so obtained compound in ether/pyridine was converted with osmiumtetroxide to 17α,17aα-dihydroxy-11α-acetoxy-D-homo-4-pregnene-3,20-dione (mp 231°–232°) which formed 11α-acetoxy-17α, 17aα-isopropylidenedioxy-D-homo-4-pregnene-3,20-dione, mp 198°–200°, by reaction with acetone in the presence of perchloric acid.

The 11α-acetoxy compound was saponified at room temperature by a methanolic solution of potassium hydroxide to obtain 11α-hydroxy-17a,17aα-isopropylidenedioxy-D-homo-4-pregnene-3,20-dione, mp 252°–258°.

b. A solution of 2.15 g of 11α-hydroxy-17α,17a-isopropylidenedioxy-D-homo-pregn-4-ene-3,20-dione and 2.2 ml of methane sulfonyl chloride in 20 ml of pyridine was maintained at 0° for 3 hours. The reaction mixture was poured into ice water and extracted with ethyl acetate. The organic extract was washed with dilute hydrochloric acid, water, sodium carbonate and several times with water, dried over sodium sulfate and evaporated to dryness under vacuum. The residue was dissolved in 100 ml of dimethlformamide, treated with 10 g of lithium chloride and heated at 100° for 90 minutes. To work up, the solution was poured into ice water and extracted with methylene chloride. The extract was washed with dilute sulfuric acid, water, sodium carbonate solution and water, dried over sodium sulfate and evaporated under vacuum. The residue was chromatographed on silica gel. The ether-hexane (1:1) eluates, which according to thin layer chromatography were homogenus fractions were purified and recrystalized from acetone-hexane to give pure 17α,17aα-isopropylidenedioxy-D-homo-pregna-4,9(11)-diene-3,20-dione, mp 150°–151°.

c. According to the conditions described in Example 1(b), 17α,17aα-isopropylidenedioxy-D-homo-4,9(11)-pregnadiene-3,20-dione was converted by N-chlorosuccinimide and perchloric acid to 9α-chloro-11β-hydroxy-17α,17aα-isopropylidenedioxy-D-homo-4-pregnene-3, 20-dione.

EXAMPLE 25

Preparation of
21-Acetoxy-9β-11β-epoxy-D-homo-1,4-pregnadiene-3,20-dione.

a. 11β,21-Dihydroxy-1,4-pregnadiene-3,20-dione (800mg) was dissolved in 8 ml of dimethylformamide, treated with 1.6 ml of acetic anhydride and 1.2 mg of lead diacetate and was stirred for 2 hours at room temperature. The product precipitated in ice water was collected by filtration, washed with water and dried. Recrystallization from acetone-hexane gave 820 mg of 11β-hydroxy-21-acetoxy-D-homo-1,4-pregnadiene-3,20-dione, mp 192°–193°.

b. 21-Acetoxy-11β-hydroxy-D-homo-1,4-pregnadiene-3,20-dione (760 mg) was dissolved in 4 ml of dimethylformamide and 0.76 ml of pyridine and 0.38 ml of methanesulfonyl chloride was added dropwise. Thereafter the mixture was stirred for 1.5 hours at 80°. The reaction mixture was cooled to about 20°, poured into ice water and dried under vacuum to obtain 650 mg of 21-acetoxy-D-homo-1,4,9 (11)-pregnatriene-3,20-dione, mp 135°–136°, after recrystallization from acetone-hexane.

c. 21-Acetoxy-D-homo-pregna-1,4,9(11)-triene-3,20-dione (374 mg) was dissolved in 9 ml of tetrahydrofuran, cooled to 0.5°, and 535 mg of N-bromosuccinimide and 3.3 ml of 1-N-perchloric acid was added dropwise. The reaction mixture was stirred at 20° for 30 minutes, poured into ice-cold sodium sulfide solution and the precipitated product was collected by filtration and dissolved in methylene chloride. The methylene chloride solution was washed with water and evaporated under vacuum to obtain 520 mg of crude 21-acetoxy-9α-bromo-11β-hydroxy-D-homo-1,4-pregnadiene-3,20-dione.

d. The crude bromohydrine (520 mg) in 25 ml of ethanol was heated under reflux for 1 hour with 1.25 g of potassium acetate. The reaction mixture was poured into ice water, the precipitated product was collected by filtration, washed with water and dried under vacuum. Recrystallization from cyclohexane afforded 320 mg of 21-acetoxy-9β,11β-epoxy-D-homo-1,4-pregnadiene-3,20-dione, mp 152°–153°.

We claim:
1. A compound of the formula

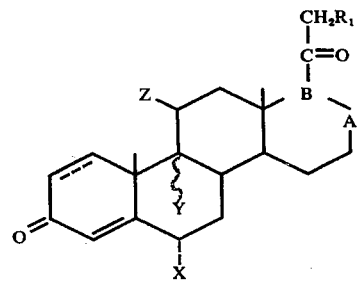

-continued wherein 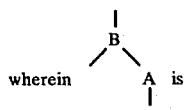 A is

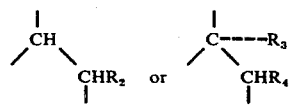

wherein $R_2$ is hydrogen or methyl, $R_3$ is hydroxy or $C_{1-8}$ alkanoic acid acyloxy, and, $R_4$ is methyl, hydroxy or $C_{1-8}$ alkanoic acid acyloxy; $R_1$ is hydrogen, fluoro, chloro, hydroxy, $C_{1-16}$ hydrocarbon carboxylic acid acyloxy, sulfato or phosphato; X is hydrogen, fluoro or methyl; Y is hydrogen and Z is alpha-hydroxy, or alpha-lower alkanoyloxy, or Z is alpha-hydroxy, alpha-lower alkanoyloxy or hydrogen when both $R_1$ and $R_2$ are substituents other than hydrogen; or Y and Z taken together is a carbon to carbon bond; and the dotted line in the 1,2-position together with the corresponding solid line denotes a single or double bond provided that there is a double bond in the 1,2-position when X and $R_2$ or X and $R_4$ each independently are hydrogen or methyl.

2. The compound of claim 1 which is 21-acetoxy-17α-methyl-D-homo-1,4,9(11)-pregnatrien-3,20-dione.

3. The compound of claim 1 which is 6α-fluoro-21-acetoxy-17α-methyl-D-homo-4-pregnene-3,20-dione.

4. The compound of claim 1 which is 6α-fluoro-21-trimethylacetoxy-17α-methyl-D-homo-1,4,9(11)-pregnatriene-3,20-dione.

5. The compound of claim 1 which is 6α-fluoro-21-acetoxy-17α-methyl-D-homo-1,4,9(11)-pregnatriene-3,20-dione.

6. The compound of claim 1 which is 17α,17aα-dihydroxy-21-acetoxy-D-homo-4-pregnene-3,20-dione.

7. The compound of claim 1 which is 17α,17aα-dihydroxy-11α-acetoxy-D-homo-4-pregnene-3,20-dione.

8. The compound of claim 1 which is 21-acetoxy-D-homo-1,4,9(11)-pregnatriene-3,20-dione.

* * * * *